US009011368B2

(12) United States Patent
Rivera-Begeman (10) Patent No.: US 9,011,368 B2
(45) Date of Patent: Apr. 21, 2015

(54) METHODS FOR IMPROVING CEREBROSPINAL FLUID FLOW

(71) Applicant: Amanda C. Rivera-Begeman, Austin, TX (US)

(72) Inventor: Amanda C. Rivera-Begeman, Austin, TX (US)

(*) Notice: Subject to any disclaimer, the term of this patent is extended or adjusted under 35 U.S.C. 154(b) by 0 days.

(21) Appl. No.: 14/037,136

(22) Filed: Sep. 25, 2013

(65) Prior Publication Data

US 2015/0088052 A1 Mar. 26, 2015

(51) Int. Cl.
*A61M 1/00* (2006.01)

(52) U.S. Cl.
CPC ............ *A61M 1/0058* (2013.01); *A61M 1/008* (2013.01); *A61M 2210/0693* (2013.01); *A61M 2202/0464* (2013.01)

(58) Field of Classification Search
CPC ............. A61M 2210/0693; A61M 2202/0464
USPC ..................................... 604/28, 506
See application file for complete search history.

(56) References Cited

U.S. PATENT DOCUMENTS

| | | | |
|---|---|---|---|
| 6,241,981 B1* | 6/2001 | Cobb et al. ............... | 424/93.1 |
| 2004/0138728 A1* | 7/2004 | Wong et al. .............. | 607/105 |
| 2008/0249501 A1* | 10/2008 | Yamasaki ................ | 604/506 |
| 2010/0226896 A1* | 9/2010 | Dracker .................. | 424/93.7 |

* cited by examiner

*Primary Examiner* — Nicholas Lucchesi
*Assistant Examiner* — Anh Bui
(74) *Attorney, Agent, or Firm* — Schwegman Lundberg & Woessner, P.A.

(57) ABSTRACT

The disclosure describes a method for improving cerebrospinal fluid flow and improving functions of the blood-cerebrospinal fluid barrier by restoring its capacity to filter toxins into cerebrospinal fluid. In some examples, the method includes accessing a cisterna magna space and withdrawing a volume of cerebrospinal fluid from the cisterna magna space. After withdrawal, the same volume of cerebrospinal fluid is infused back into the cisterna magna space to exert pressure, which is transmitted as kinetic energy to the membrane of the blood-CSF barrier. This re-establishes the membrane with a proper electrochemical potential difference such that normal filtration mechanisms resumes with ongoing CSF production.

20 Claims, 5 Drawing Sheets

METHODS FOR IMPROVING CEREBROSPINAL FLUID FLOW

BACKGROUND

The present disclosure relates generally to methods for improving cerebrospinal fluid flow, and more particularly, relates to such methods wherein functions of the blood-cerebrospinal fluid barrier are improved by restoring its capacity to filter toxins into cerebrospinal fluid.

Cerebrospinal fluid (CSF) is produced primarily in the choroid plexus of the brain and acts as a cushion and buffer by providing mechanical and immunological protection to the central nervous system. Further, CSF acts as a transport medium for nutrients, neuroendocrine substances and for the removal of toxic metabolites, preserving the chemical environment of the brain. The central nervous system requires a stable environment to function normally. This stability is provided, at least in part, by isolating the central nervous system from blood with a blood-CSF barrier. Under normal conditions, the blood-CSF barrier functions as a semipermeable barrier that protects the brain and spinal cord from potentially harmful substances while permitting gases and nutrients to enter nervous tissue. Water, gases, and lipid-soluble substances freely pass from the blood to the cerebrospinal fluid. Macromolecules such as proteins and most hexoses other than glucose are unable to enter the cerebrospinal fluid.

CSF flows throughout the ventricular system in the brain and is absorbed back into the bloodstream, rinsing metabolic waste from the central nervous system. This allows for homeostatic regulation of the distribution of neuroendocrine factors, to which slight changes can cause problems or damage to the nervous system. The CSF performs a sink action by which the various substances formed in nervous tissue during its metabolic activity diffuse rapidly into the CSF and are thus removed into the bloodstream as CSF is absorbed. The accumulation of any substance transported through the CSF is controlled to a large extent by the pulsatile dynamics of CSF. It has been determined that an accumulation of toxins at the blood-CSF barrier and abnormal CSF flow are contributors to the pathogenesis of neurodegenerative disorders, such as Alzheimer's, Autism, Amyotrophic lateral sclerosis, and traumatic brain diseases, through the accumulation of toxic metabolites, through the disruption of neuroendocrine communication or through any combination of these factors.

The presence of very small, even negligible, dosages of certain chemicals acting in conjunction with the body has been observed to have significantly negative effects on brain functions. Detoxification of bodily systems may effectively lead to amelioration or recovery from disorder symptoms. A properly functioning blood-CSF barrier facilitates the filtering of toxic metabolites into the CSF and transports nutrients/chemical messengers from secreted CSF to target cells, allowing the brain to operate at higher capacities. For example, with Autism, a restoration of the blood-CSF barrier to normal functions leads to higher levels of alertness and neurologic function for individuals affected by the disorder.

Current attempts to improve neurologic functions are focused on the development of synthetic drugs or exogenously manipulating CSF flow, which have not been successful in the treatment of neurologic disorders. Further, individuals affected with such disorders are often subject to defects in many other organ systems other than the brain. For example, oxidative stresses have been observed virtually every organ system assessed in individuals diagnosed with Autism. The intake of or exposure to synthetic drugs further stresses organ systems and causes unintended side effects, which may result in detrimental and potentially irreversible damage (e.g., liver or kidney damage due to excessive strain placed on the organs from filtering synthetic drugs). A method for treating neurologic disorders without using synthetic drugs would prevent further burdening the organs, including the brain, of individuals that already have difficulty processing and eliminating toxins (e.g., toxins originating from an external environment, including synthetic drugs, and toxins produced within an individual's body).

DETAILED DESCRIPTION

The following detailed description refers to the accompanying drawings that depict various details of examples selected to show how particular embodiments may be implemented. The discussion herein addresses various examples of the inventive subject matter at least partially in reference to these drawings and describes the depicted embodiments in sufficient detail to enable those skilled in the art to practice the invention. Many other embodiments may be utilized for practicing the inventive subject matter than the illustrative examples discussed herein, and many structural and operational changes in addition to the alternatives specifically discussed herein may be made without departing from the scope of the inventive subject matter.

In this description, references to "one embodiment" or "an embodiment," or to "one example" or "an example" mean that the feature being referred to is, or may be, included in at least one embodiment or example of the invention. Separate references to "an embodiment" or "one embodiment" or to "one example" or "an example" in this description are not intended to necessarily refer to the same embodiment or example; however, neither are such embodiments mutually exclusive, unless so stated or as will be readily apparent to those of ordinary skill in the art having the benefit of this disclosure. Thus, the present disclosure includes a variety of combinations and/or integrations of the embodiments and examples described herein, as well as further embodiments and examples as defined within the scope of all claims based on this disclosure, as well as all legal equivalents of such claims.

This disclosure describes a method for improving cerebrospinal fluid flow and improving functions of the blood-cerebrospinal fluid barrier by restoring its capacity to filter toxins into cerebrospinal fluid. In some examples, the method includes accessing a cisterna magna space and withdrawing a volume of cerebrospinal fluid from the cisterna magna space. After withdrawal, the same volume of cerebrospinal fluid is infused back into the cisterna magna space to exert pressure, which is transmitted as kinetic energy to the membrane of the blood-CSF barrier. This re-establishes the membrane with a proper electrochemical potential difference such that normal filtration mechanisms resumes with ongoing CSF production.

Figure 1A:
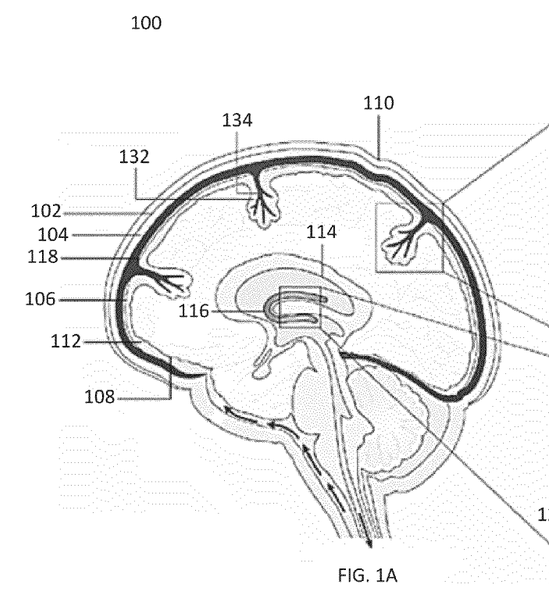
FIGS. 1A-1C illustrate example diagrams of the central nervous system where cerebrospinal fluid is produced.
Figure 1B:
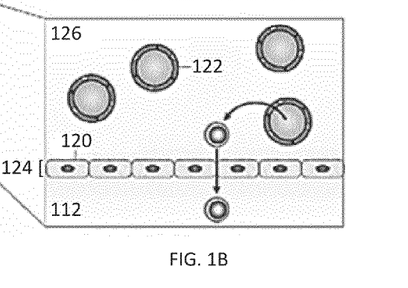
Figure 1C:
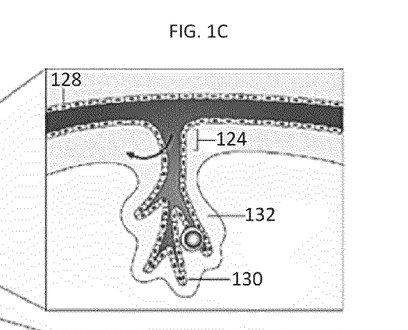

Referring now to FIGS. 1A-1C, these figures illustrate example diagrams of the central nervous system where cerebrospinal fluid is produced. In the central nervous system 100, the brain and spinal cord are surrounded by a system of membranes, generally referred to as the meninges 102, which comprises three layers: the dura mater 104, the arachnoid mater 106, and the pia mater 108. The brain and spinal cord are protected by the skull bones 110 and vertebral column. Further protection is provided by the cerebrospinal fluid, which surrounds the brain and spinal cord in the subarachnoid space 112 (e.g., the space between the arachnoid mater 106 and the pia mater 108). The cerebrospinal fluid is also located in ventricles 114 of the brain. Cerebrospinal fluid is contained and continuously circulates within both the ventricles 114 and the meninges 102 (e.g., in the subarachnoid space 112).

Figure 2:
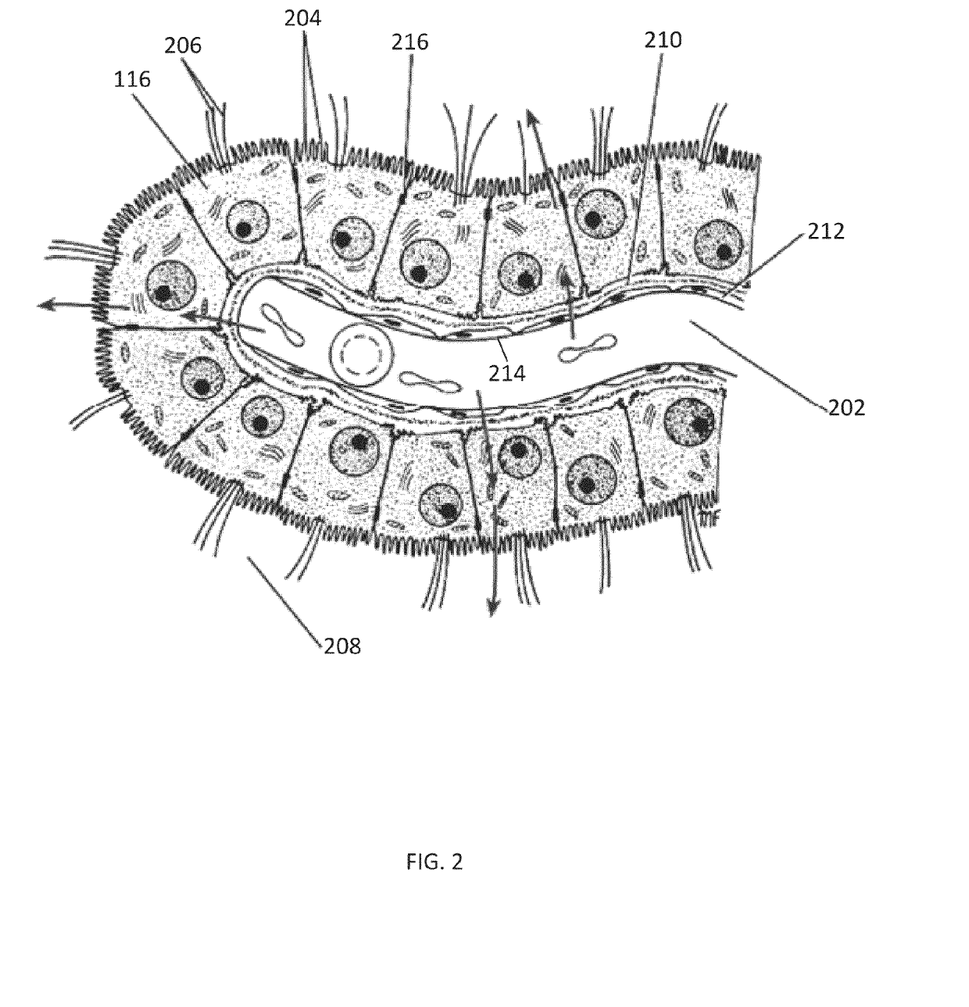
FIG. 2 depicts a zoomed-in illustration of the blood-CSF barrier.

The cerebrospinal fluid, which bathes the external and internal surfaces of the brain and spinal cord, serves as a cushion between the central nervous system 100 and the surrounding bones, protecting it against mechanical trauma by providing mechanical support for the brain and regulating inter-cranial pressure. CSF is produced primarily at the choroid plexus 116 (approximately 50-70% of total volume) of all ventricles in the brain, as well as at the choroid plexus in the cisterna magna and by ependymal cells around blood vessels 118. The choroid plexus 116 is comprised of clusters of capillary blood vessels in the ventricular system and has a folded surface (as shown in FIG. 2), with each fold consisting of a core of vascular connective tissue from the pia with cuboidal epithelial cells 120 (e.g., ependymal cells) from the ventricles that are connected to each other by tight junctions. As illustrated in FIG. 1B, the epithelial cells 120 are fenestrated and permeable to large molecules 122, which can enter the subarachnoid space 112 by crossing the blood-CSF barrier 124 surrounding the choroid plexus stroma 126.

As shown in FIG. 1C, molecules 122 can also enter the subarachnoid space 112 by crossing the walls of meningeal blood vessels in the brain, which consist of endothelial cells 128 connected by tight junctions, with the membranes of adjacent cells are almost fused with each other. Molecules 122 can cross the blood-brain barrier 130 surrounding post-capillary venules 134 to enter the perivascular space 132, which is the region between the basement membrane connected to blood vessel endothelial cells 128. This barrier is only slightly permeable to $Na^+$, $Cl^-$, $K^+$ and large organic molecules. This makes it difficult to achieve effective concentrations of antibodies or non-lipid-soluble drugs in the brain and creates a low permeability barrier between the blood-brain and between the CSF-brain.

A zoomed-in illustration of the blood-CSF barrier 124 is provided in FIG. 2. The blood-CSF barrier 124 at the choroid plexus 116 comprises a one-cell layer of epithelial cells that is circumferentially arranged around a choroidal capillary 202. The choroid plexus 116 is a vascular tissue found in all cerebral ventricles. Unlike the capillaries that form the blood-brain barrier, choroidal capillaries are fenestrated and have no tight junctions. The choroidal capillary 202 endothelium, therefore, does not form a barrier to the movement of small molecules. The free surfaces of the epithelial cells are covered with microvilli 204 and cilia 206. The blood within the choroidal capillary is separated from a lumen 208 of a ventricle by: the epithelial cells, which are fenestrated and have thin walls; a continuous basement membrane 210 surrounding the choroidal capillary 202 outside the endothelial cells 212 of the choroidal capillary 202; scattered pale cells 214 with flattened processes; and the continuous basement membrane 210, on which rest the epithelial cells of the choroid plexus 116. The blood-CSF barrier 124 is located between the lumen of the choroidal capillary 202 and the lumen 208 of the ventricle where CSF flows. Tight junctions 216 between the choroidal epithelial cells assist in performing the functions of the blood-CSF barrier 124.

The choroid plexus 116 actively secretes cerebrospinal fluid, which generates a small pressure gradient. At the same time, the choroid plexus 116 actively transports nervous system metabolites from the cerebrospinal fluid into the blood, leading to lower concentrations of potassium, calcium, magnesium, bicarbonate, and glucose in the cerebrospinal fluid than in the blood. CSF possesses, in solution, inorganic salts similar to those in blood plasma. The glucose content is about half that of blood (e.g., 50-85 mg/100 ML), and contains only a trace amount of protein (e.g., 15-45 mg/100 mL, depending on sampling site). Only a few lymphocyte cells are present (e.g., the normal lymphocyte count is 0-3 cells per cubic millimeter). In the lateral recumbent position, the pressure, as measured by spinal tap, is about 60-150 mm $H_2O$ and similar to the intracranial pressure. The pressure of the cerebrospinal fluid shows oscillations corresponding to the movements of respiration and the arterial pulse, but remains relatively constant.

Figure 3:
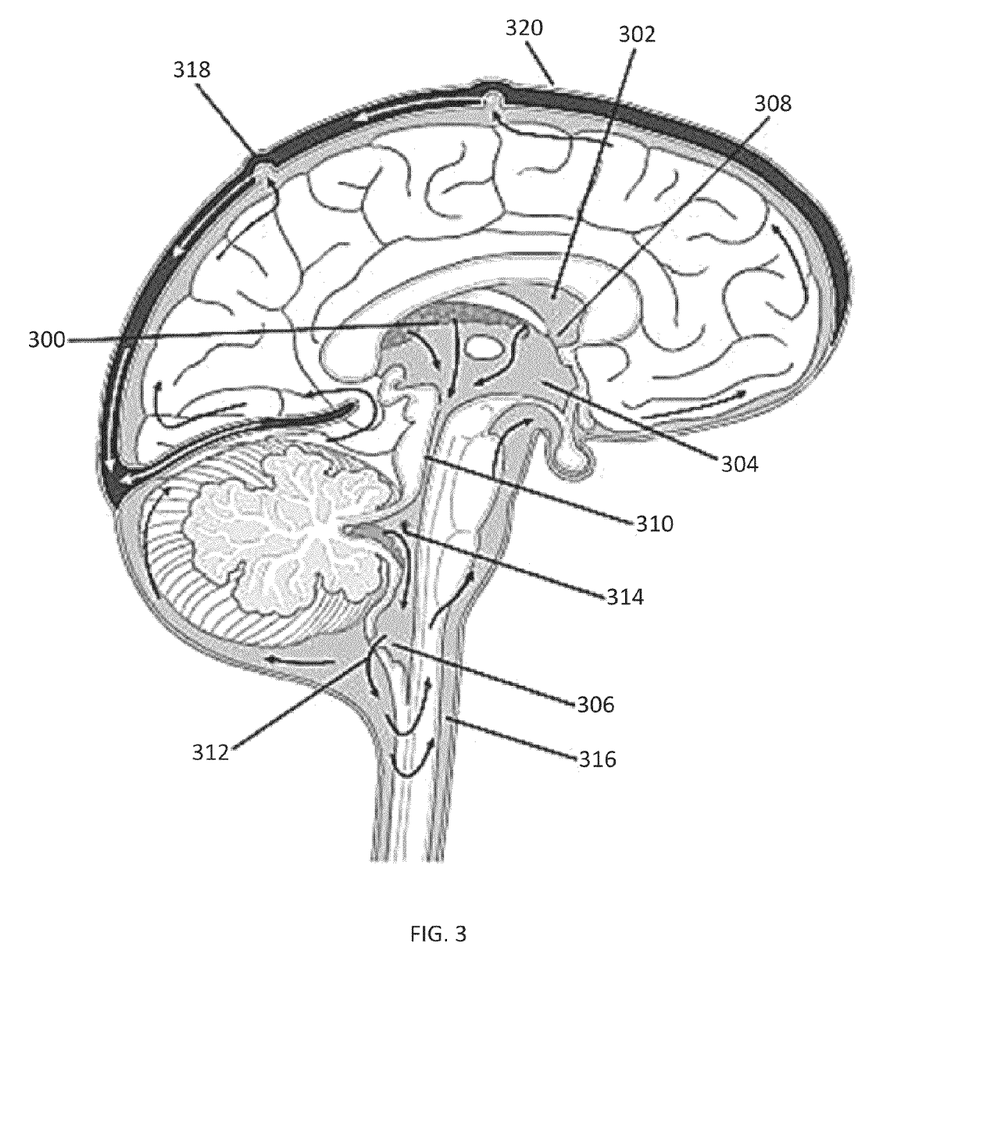
FIG. 3 illustrates a diagram of a cerebrospinal fluid circulation within the central nervous system.

Cerebrospinal fluid is produced and circulates within the central nervous system, as depicted by the arrows in the diagram of FIG. 3. CSF circulates in two different compartments: inner brain ependymal cavities (ventricles) and compartment surrounding the central nervous system (subarachnoid space). Cerebrospinal fluid is continuously produced by choroid plexuses 300 in the lateral ventricle 302, third ventricle 304, and fourth ventricle 306 of the brain. CSF production includes both: passive filtration of fluid across choroidal capillary endothelium and active secretion across single-layer epithelial cells of the choroid plexuses 300. CSF circulation begins with its secretion from the choroid plexuses 300 in the ventricles 302, 304, and 306. The CSF passes from the lateral ventricle 302 into the third ventricle 304 through the interventricular foramina 308. CSF then passes into the fourth ventricle 306 through the cerebral aqueduct 310. The circulation is aided by the arterial pulsations of the choroid plexuses 300 and by cilia on the ependymal cells lining the ventricles. From the fourth ventricle 306, the CSF passes slowly through the Foramen of Magendie (median aperture) 312 and the Foramen of Luschka (lateral aperture) 314 of the lateral recesses of the fourth ventricle 306 to enter the subarachnoid space 316 (e.g., principal openings, termed cisterns, such as the cisterna magna), where the CSF bathes external surfaces of the brain and spinal cord.

The CSF system is multi-compartmental, with the ventricles, cisterns, and subarachnoid spaces being serially linked. After entering the subarachnoid space 316, CSF moves through the cerebellomedullary cistern and pontine cisterns and flows superiorly through the tentorial notch of the tentorium cerebelli to reach the inferior surface of the cerebrum. CSF moves superiorly over the lateral aspect of each cerebral hemisphere, assisted by the pulsations of the cerebral arteries. Some of the cerebrospinal fluid moves inferiorly and circulates in the subarachnoid space around the spinal cord. The CSF flows in a downward direction posterior to the spinal cord and in an upward direction anterior to the spinal cord. Here, the fluid is at a dead end, and its further circulation relies on the pulsations of the spinal arteries and the movements of the vertebral column, respiration, coughing, and the changing of the positions of the body.

The main sites for the absorption of the cerebrospinal fluid into venous sinus blood are arachnoid villi, which tend to be grouped together to form arachnoid granulations 318, that project into the dural venous sinuses, especially at the superior sagittal sinus 320. Further, some of the cerebrospinal fluid is absorbed directly into the veins in the subarachnoid space. The arachnoid villi function like one-way valves to allow the CSF into the venous blood of the dural venous sinuses, but do not allow the blood to flow in the opposite direction.

The absorption of cerebrospinal fluid into the venous sinuses occurs when the cerebrospinal fluid pressure exceeds the venous pressure in the sinus, allowing for a direct flow of fluid from the subarachnoid space into the lumen of the venous sinuses. Generally, the arachnoid villi valves open approximately at a pressure of 1.5 mm Hg greater than the pressure of the blood within the sinuses. Should the venous pressure rise and exceed the cerebrospinal fluid pressure, compression of the tips of the villi closes and prevents the reflux of blood into the subarachnoid space. CSF pressure is regulated almost entirely by the arachnoid villi. Because the production of cerebrospinal fluid from the choroid plexuses is constant, the rate of absorption of cerebrospinal fluid through the arachnoid villi controls the cerebrospinal fluid pressure.

CSF moves in a pulsatile manner throughout the CSF system with nearly zero net flow. Arterial pulsations cause the CSF to flow with a small pulsatile movement towards the superior sagittal sinus 320 with each heartbeat. The CSF is produced continuously at a rate of 500-700 mL per day. Since the subarachnoid space 316 around the brain and spinal cord generally contain only a volume of approximately 150 mL, the CSF turns over approximately three to five times a day. Production of cerebrospinal fluid is not pressure regulated (as in the case of blood pressure), and continues to be produced even if the reabsorption mechanisms are obstructed. When CSF pressure is elevated, cerebral blood flow may be constricted. When disorders of CSF flow occur, they may therefore affect not only CSF movement but also craniospinal compliance and the intracranial blood flow, with subsequent neuronal and glial vulnerabilities.

As previously discussed, one function of the CSF is to mechanically support the central nervous system. The close relationship of the CSF to the nervous tissue and the blood enables it to serve as a reservoir and assist in the regulation of the contents of the skull. For example, if the brain volume or the blood volume increases, the cerebrospinal fluid volume decreases. A second function of the cerebrospinal fluid occurs in concert with metabolism. Since the cerebrospinal fluid is an ideal physiologic substrate, it also plays an active part in the nourishment of nervous tissue and assists in the removal of products of neuronal metabolism by regulating the exchange of substances between the blood and the CSF. There are no lymphatics within the central nervous system and the CSF largely performs the function carried out by lymph in other tissue. CSF is involved in the removal of the waste products of cerebral metabolism, primarily $CO_2$, lactate and excess $H^+$ ions. The CSF also serves as a route for the conduction of neuron-active peptides and hormones and also helps to provide a stable chemical environment for cerebral and spinal neurons.

Figure 4:
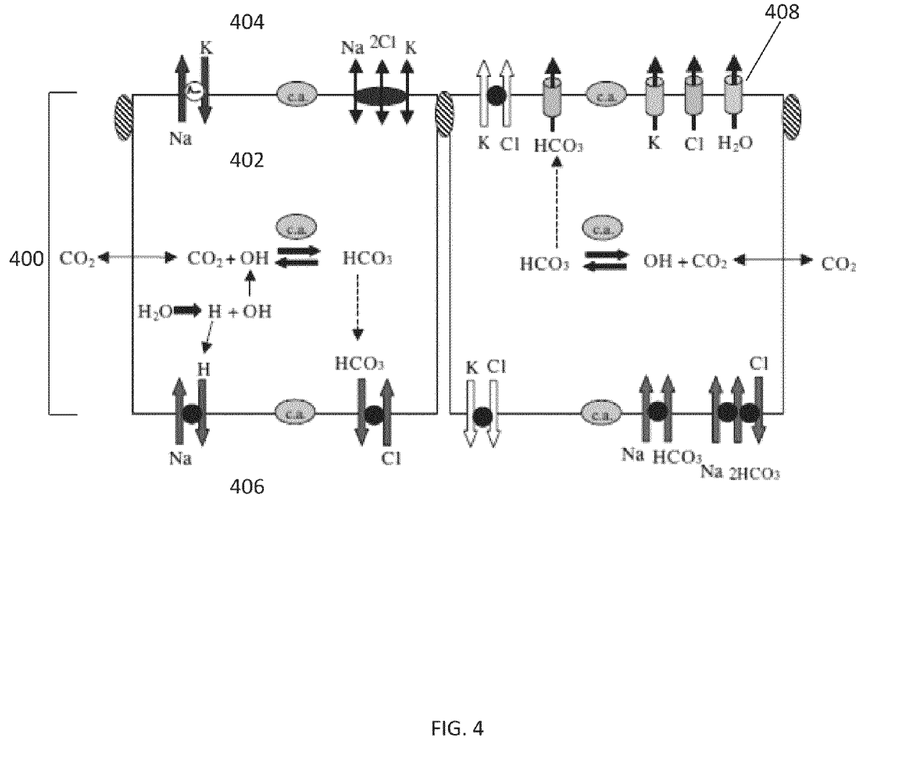
FIG. 4 provides a diagram of an example model of CSF secretion due to ion transport across the choroid plexus epithelium.

FIG. 4 provides a diagram of an example model of CSF secretion due to ion transport across the choroid plexus epithelium. CSF production begins as blood plasma is filtered across the permeable choroidal capillaries. CSF is actively produced by the coordinated secretion of solutes across the epithelial cell 400 interface between the inner choroidal plasma 402 and outer ventricular fluid 404. Ions and water are taken up by facilitating mechanisms at the juncture of capillary blood 406 and choroidal plasma 402, transferred through the cytoplasm of the epithelial cell 400, and then released or actively secreted into ventricular fluid 404 in the ventricles. Trans-choroidal secretion of ions, water and macromolecules drives the volumetric transmission of CSF along the ventricular system. Net filtration may be proportional to the hydrostatic pressure gradient between capillary blood 406 and choroidal plasma 402.

The secretion of cerebrospinal fluid occurs mainly by active transport of $Na^+$ ions through the choroid plexus epithelium. The $Na^+$ ions are closely followed by $Cl^-$, $K^+$, and $HCO_3$ ions which follow along with $H_2O$. Electrochemical gradients favor the movement of $Na^+$ ions inward from the capillary blood 406 into the choroidal plasma 402, and then into ventricular fluid 404 in the ventricles. Further, electrochemical gradients favor the outward diffusion of $Cl^-$, $K^+$, and $HCO_3$ ions from the choroidal plasma 402 into ventricular fluid 404 in the ventricles. Water flux is provided by aquaporin channels 408 that osmotically balance ion transport and provides the medium for CSF circulation. CSF production by the choroid plexus is driven by active ion transport that results in a net secretion of $Na^+$ and $Cl^-$, the main ionic constituents of CSF. Re-absorption of ions from CSF to blood occurs simultaneously with active secretion but overall, there is net movement of ions and water into the ventricular fluid 404 in the ventricles.

The fine-regulation of the composition and the free-flow of CSF are vital to brain health. Disruption of CSF flow, such as disease-induced changes to CSF circulation, may adversely affect central nervous system functions and lead to diminished cognitive and motor functions. Choroid plexus and CSF dynamics may become distorted, for example, substance transport and removal of toxic metabolites might be disrupted. Different areas of the brain may be affected dissimilarly by a disruption to CSF flow. As an example, a brain region requiring very efficient flushing of toxic metabolites may experience accumulation of waste products that could lead to or accelerate neurodegenerative processes, whereas, in other areas, the disruption may have little to no effect. In some areas the toxins might accumulate, while in others the toxins might not, which may lead to neurodegenerative conditions. Further, decreased cerebrospinal fluid flow may lead to pathological increases in plasma protein concentration in the cerebrospinal fluid.

Due to the interconnected nature of the CSF system, diffusion and bulk flow of solutes within CSF depend upon prevailing regional gradients for concentration and hydrostatic pressure in various fluid compartments of the CSF system. Upstream CSF transport phenomena may exert effects downstream. Thus, attempts have been made to use CSF-borne therapeutic agents to manage ventricular dysfunctions and neurodegenerative disorders. However, existing pharmacological methods for rectifying CSF disorders may be ineffective, especially in debilitated CSF systems wherein the introduction of drugs would further strain choroidal and CSF functions.

The mechanisms behind the circulation of cerebrospinal fluid may be described as a semi-closed, hydraulic system (e.g., Pressurestat Model), wherein fluid may be introduced and removed from a container, via regulated inflow and outflow mechanisms, with controlled rates of flow. The cerebrospinal fluid represents the fluid that is contained within the meninges (e.g., closed container). The inflow pumping system comprises the choroid plexuses in the various ventricles of the brain. The outflow system comprises the reabsorption of CSF back into venous blood at the arachnoid granulations, which have the ability to increase or decrease the general rate of reabsorption of CSF within the system based on CSF pressure. Thus, the meninges (especially the dura mater) form the functional boundary of the hydraulic system, and the cerebrospinal fluid forms the hydraulic part. Transmission of pressure occurs according to the law of fluid mechanics—any force to the CSF surface is transmitted equally in all directions within the boundaries of the system.

Unimpaired CSF flow is critical; if an area of brain tissue is even partially deprived of optimal CSF motion and flow, that area may be forced into some degree of functional compromise. In one embodiment, the present disclosure describes mechanical methods for restoring normal filtration mechanisms at the choroid plexus and improving CSF production. Imbalances in the production, circulation, and reabsorption of cerebrospinal fluid can negatively influence performance of the brain and spinal cord, resulting in any number of a variety of sensory, motor or neurological disorders. One skilled in the art will readily recognize that although described specifically in connection with application of the methods for Autism, the embodiments described herein are similarly applicable to any condition that leads to a buildup of toxins at the level of the blood-CSF barrier, including Alzheimer's disease, Amyotrophic lateral sclerosis, and various traumatic brain diseases. Similarly, the methods are applicable to any disorders associated with decrease CSF production or circulation. These may include primary and secondary neurological disorders that have yet to be identified, but are associated with the same above discussed pathologies.

Figure 5:
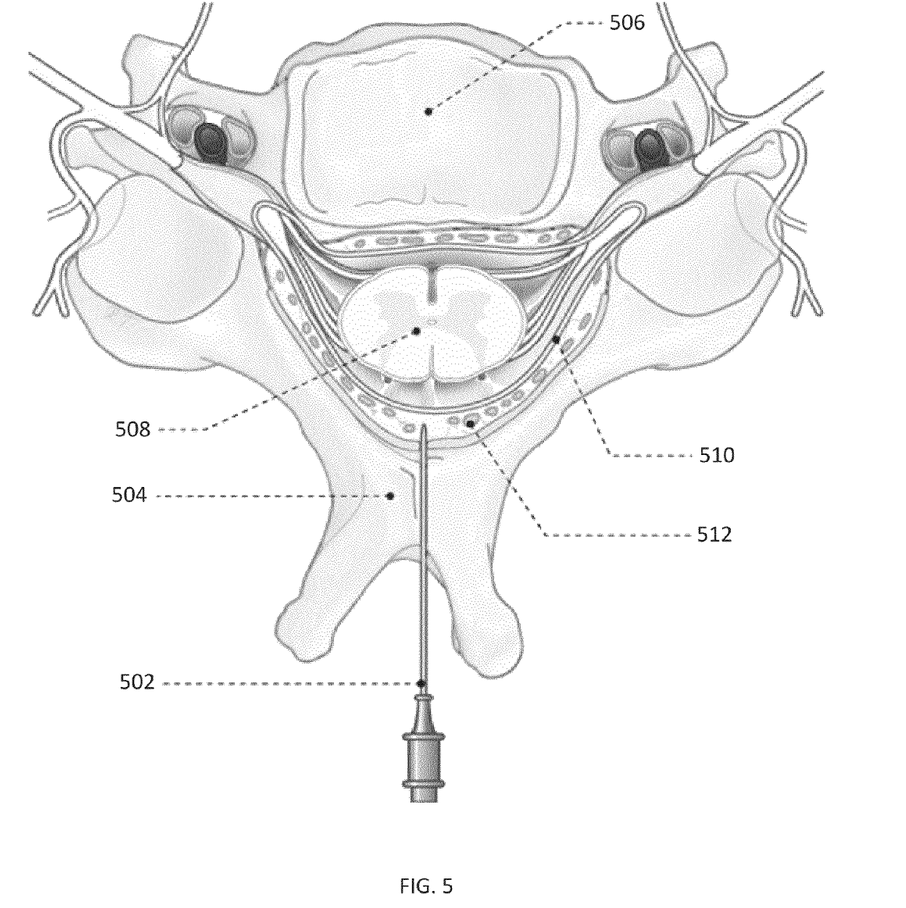
FIG. 5 shows an example procedure for improving cerebrospinal fluid flow, showing vertebrae as seen from above.

FIG. 5 shows an example procedure for improving cerebrospinal fluid flow, showing vertebrae as seen from above. In an embodiment, a patient may be prepared for the procedure to alter cerebrospinal fluid flow. For example, the skin at an injection site may be locally anesthetized. A cervical puncture procedure may be performed, wherein the tip of a needle or catheter 502 is inserted between individual vertebrae 504 of the vertebral column 506, between which inter-vertebral discs allow movement of the vertebrae 504 relative to one another. The spinal cord lies within the spinal canal 508 and is surrounded by cerebrospinal fluid, and is further surrounded by the dura mater 510 of the meninges. The epidural space 512 lies between the dura mater 510 membrane and the hard bone of the vertebrae 504. The cervical puncture not only allows access to the CSF but also to the cisterna magna, wherein the subarachnoid space, the arachnoid and pia mater layers of the meninges surround the brain. In a different example, ventricular space within the ventricles of the brain may be accessed by the needle. An abundance of choroid plexus (primary blood-CSF barrier) is located in the fourth ventricle, proximal to the foramen of Magendie.

Lateral cervical puncture procedures may be performed with intrathecal puncture at level C0-C1 (between the occiput and the C1 arch) to access the cisterna magna in the subarachnoid space. Puncture at this level represents a lateral puncture of the cisterna magna. It is well known that the subarachnoid space between the arch of C1 and the occiput shows substantial extension, with the posterior border corresponding to the connecting line between the posterior edges of the foramen magnum to the arch of C1. Above the level of the C1 arch, there is an increase in distance between the posterior surface of the spinal cord to the posterior border of the subarachnoid space. The volume of subarachnoid space at this level exceeds the subarachnoid space at the C1-C2 level. Navigating the needle in the posterior part of the subarachnoid space at the C0-C1 level may prevent any unfavorable touching of the spinal cord. In another embodiment, the puncture may be performed at the C1-C2 level.

However, the lateral approach at the C0-C1 level includes at least two advantages: 1) there are less adverse effects than the C1-C2 level puncture because it avoids potential direct needle contact to the spinal cord surface. If a strong sagittal position of the head is ensured, it becomes more difficult for the needle to reach the spinal cord because its trajectory lies posterior to the spinal cord surface, allowing for more precise navigation; 2) the C0-C1 level puncture gives skilled individuals the option to apply this intrathecal puncture in rooms without fluoroscopy (e.g., intensive care for diagnostic purposes, or direct in the CT room). In such cases, the needle should be inserted in a point approximately 2-2.5 cm posterior to the mastoid apex in a virtual line parallel to the orbitomeatal line. The needle may be advanced with slowly successive movements, sliding the posterior surface of the occiput to the point of penetration of the dura mater in the lateral and posterior parts of the suboccipital cisterna magna. A pop may be felt as the needle penetrates the dura mater.

In another embodiment, a lumbar puncture (e.g., spinal tap) may be performed, instead of a cervical puncture, to access the cerebrospinal fluid. The spinal cord terminates inferiorly at the level of the lower border of the first lumbar vertebra in adults, and in infants, the spinal cord may reach inferiorly to the third lumbar vertebra. The subarachnoid space extends inferiorly as far as the lower border of the second sacral vertebra. The lower lumbar part of the vertebral canal is thus occupied by the subarachnoid space, which contains the lumbar and sacral nerve roots. A lumbar puncture needle introduced into the subarachnoid space in this region usually pushes the nerve roots to one side without causing damage. The lumbar puncture needle, fitted with a stylet, may be inserted into the vertebral canal above or below the fourth lumbar spine. The depth to which the lumbar puncture needle penetrates varies from 1 inch (2.5 cm) or less in a child to as much as 4 inches (10 cm) in an obese adult. However, a lumbar puncture does not provide proximate access to choroid plexus tissue. A long catheter may be guided with fluoroscopic guidance up to the cisterna magna, where the blood-CSF barrier is located.

In another embodiment, a suboccipital puncture (cisternal puncture) may be performed, instead of a cervical puncture, to access the cerebrospinal fluid. The suboccipital puncture is performed by inserting a needle through the skin below the external occipital protuberance into the cisterna magna, and is an alternative to lumbar puncture. Subarachnoid hemorrhage and direct puncture of brain tissue or vascular structures are the most common major complications, therefore, fluoroscopic guidance is recommended to decrease the risk of complications. If the entering needle should stimulate one of the nerve roots, the patient may experience a discomfort in one of the dermatomes or a muscle will twitch, depending on whether a sensory or a motor root was impaled. The contraindications to suboccipital and lumbar punctures are similar as those to those of cervical punctures.

The stylet is removed after the needle has accessed the cisterna magna, a subarachnoid space, or a ventricular space. As the stylet is withdrawn, a few drops of blood may escape. This usually indicates that the point of the needle is situated in one of the veins of the internal vertebral plexus and has not yet reached the subarachnoid space. A stopcock may be attached to an end of the needle to restrict the flow of cerebrospinal fluid. The stopcock includes at least one point for the attachment of a syringe for collection of CSF. The stopcock may include additional points for the attachment of a manometer for reading CSF pressure or co-injection of additives. A pre-designated volume of cerebrospinal fluid is withdrawn with a syringe and infused back into the same space at a pre-designated rate. The terms "remove" and "withdraw" are synonymous with "efflux" of CSF from the patient. In an embodiment, the withdrawn cerebrospinal fluid may be reconstituted into a cerebrospinal fluid mixture by mixing the volume of cerebrospinal fluid with an additive prior to infusing the volume of cerebrospinal fluid back into the space from which it was withdrawn (e.g., cisterna magna space). The additive may include at least one of a volume of stem cells, synthetic drugs, non-synthetic drugs, and supportive nutrients. Additionally, before the CSF or CSF-additive mixture is re-infused, a sample of CSF may be collected for lab testing or direct visualization under a microscope (e.g., immediate assessment by a pathologist or other qualified medical staff).

As previously mentioned, once the catheter is positioned within the cisterna magna, an amount of CSF is withdrawn into an attached sterile syringe and re-infused back into the cisterna magna (either alone or mixed with stem cells as needed). The terms "re-insert" and "re-infuse" may be used interchangeably, describing the act of putting the patient's CSF or CSF-additive mixture back into the cisterna magna. Similarly, "influx" may be used to describe the act of putting the patient's CSF or CSF-additive mixture back into the cisterna magna. A pressure exerted is through the syringe and needle to re-infuse the CSF, wherein the influx of CSF causes rapidly increased flow of the CSF in the cisterna magna. This rapid increase in CSF flow acts as a hydraulic fluid in a semi-closed hydraulic system and transmits the kinetic energy associated with the influx of CSF to the semi-permeable membrane of the blood-CSF barrier.

The blood-CSF barrier, which is a semipermeable membrane, normally maintains an electrical voltage, due to an ionic potential difference between the two sides of the membrane. Neurotoxins and neuro-inflammatory mediators that make it to the blood-CSF barrier accumulate there and cause increasing resistance to normal ionic flow at the membrane. When this occurs, the membrane of the blood-CSF barrier is impaired and does not function as it should. The end result in persons at risk for autism is decreased alertness and function in all activities of daily living. The kinetic energy from the CSF influx transmits to the adjacent blood-CSF barrier of the meninges and choroid plexus as an electrochemical potential difference (e.g., increased voltage) across voltage gated ion channels. This kinetic energy is converted to potential energy and causes a rapid shift in the ions across the semi-permeable membrane, thereby re-establishing the membrane with an electrochemical potential difference.

Re-establishing the electrochemical potential difference across the blood-CSF barrier membrane at the choroid plexus so that it can properly perform as a filter for the brain to flush out endogenous and exogenous toxic wastes. Once the normal filtration mechanism is re-established, the normally pulsatile CSF flow will propagate the created potential energy from the filtration of toxic substances and turn that potential energy into kinetic energy as CSF circulates. The kinetic energy passes through CSF to encounter downstream ependymal cells for drainage and elimination. The kinetic energy then re-establishes the electric-potential energy at the membranes of the downstream ependymal cells.

This cycle of converting potential energy to kinetic energy and back again to potential energy (as toxic waste is properly filtered) keeps the system running on its own, assuming no further neurotoxic insults to the blood-CSF barrier. The total work (sum of potential energy and kinetic energy) produced by the proper flow of CSF, established by a well-functioning blood-CSF barrier (acting as a hydraulic system), provides the energy needed for toxins to exit ependymal cells of the blood-CSF barrier. An additional benefit is that it also provides the energy needed for nutrients (including exogenous stem cells) to enter the brain through the endothelial cells of the CSF-brain barrier. Further, by improving downstream CSF flow, drainage from the CSF system is improved with increased recycling of toxin-laden CSF, thereby increasing removal of endogenous and exogenous toxic wastes out of CSF into venous blood and increasing the frequency that nutrients or chemical messengers secreted into the CSF are brought to their target cells.

To support elimination of endogenous or exogenous toxins with the aim of limiting further neurotoxic insults, allowing a sufficient passage of time for neural stem cells (endogenous or exogenous) to repair any damage, and preventing the blood-CSF barrier from corroding again, it is expected that the patient will be on a diet that supplies enough nutrients to promote the body's natural detoxification mechanisms (e.g., intake of foods containing precursors for glutathione production in the liver).

Measurements of CSF volume and CSF flow rate may be used to diagnose dysfunctions of blood-CSF barrier and then effectiveness of treatment. Phase-contrast MR studies can calculate CSF volume and CSF flow rate before the procedure is applied. Subsequently, an intraoperative MRI (iMRI) may be employed to determine if the procedure has been successful in increasing CSF flow rate. iMRI may also be used to determine if multiple trials need to be done within a single procedure.

In mild cases of Autism, the influx of CSF stimulates the production of neural stem cells that are normally in the periventricular brain tissue to repair the damaged blood-CSF barrier. As long as the periventricular region is not damaged, the influx of CSF stimulates the release of neural stem cells and initiates repair with the body's own endogenous stem cells. However, in more advanced cases where there is damage to areas of the brain that normally produce neural stem cells, the infusion of a CSF-additive mixture including exogenous stem cells will act as reparative agents to target the damaged areas for repair. The infused stems cells, which may further comprise supportive nutrients, further aids the restoration process of the blood-CSF barrier functions.

In some embodiments, the CSF infusion procedure may be employed as a plurality of injections over a period of time. A port may be inserted under the skin with a hollow tube that leads to the space needed. For example, a sub-occipital port may be inserted which provides access to the CSF in the cisterna magna, adjacent to the choroid plexus in the 4th ventricle. This allows for subsequent extraction of CSF from the port without requiring additional punctures and further allows for infusion. Further, the ports may be used as an access point to the cisterna magna for delivering any additional substances (e.g., synthetic drugs). In another embodiment, extracted CSF may be exogenously filtered (e.g., CSF dialysis) before the CSF is re-infused back into the cisterna magna.

Although the present disclosure describes the efflux and influx of CSF to re-establish blood-CSF barrier functions, one skilled in the art would recognize that additional compounds may be introduced by injection into the subarachnoid space of the central nervous system in place of CSF. For example, various compounds (including stem cells or synthetic drugs) may be suspended in a sterile buffer or carrier compatible with cerebrospinal fluid (e.g., a sterile physiological preservative-free saline solution) and administered to the patient as a bolus injection or as a continuous, constant-rate epidural infusion.

Although the present invention has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

Although an embodiment has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for altering cerebrospinal fluid flow, comprising the steps of:
    accessing a cisterna magna space containing cerebrospinal fluid;
    withdrawing a volume of cerebrospinal fluid from the cisterna magna space; and
    infusing the volume of cerebrospinal fluid back into the cisterna magna space as a bolus injection at a rate capable of transmitting a boost in kinetic energy to a blood-CSF barrier, wherein the boost in kinetic energy is converted into potential energy and causes a change in an electrochemical potential difference that facilitates transcellular mechanisms across the blood-CSF barrier for improving at least a blood filtration or a CSF production function of the blood-CSF barrier.

2. The method of claim 1, wherein the step of accessing a cisterna magna space comprises performing a lateral cervical puncture.

3. The method of claim 2, further comprising fluoroscopically guiding a catheter into the cisterna magna space.

4. The method of claim 1, wherein the step of accessing a cisterna magna space comprises performing a sub-occipital cervical puncture.

5. The method of claim 1, wherein the step of accessing a cisterna magna space comprises performing a lumbar puncture and guiding a catheter into the cisterna magna space.

6. The method of claim 1, further comprising the step of preparing a cerebrospinal fluid mixture by mixing the volume of cerebrospinal fluid with an additive prior to infusing the volume of cerebrospinal fluid back into the cisterna magna space.

7. The method of claim 6, wherein said additive comprises at least one of a volume of stem cells, synthetic drugs, non-synthetic drugs, and supportive nutrients.

8. The method of claim 1, wherein the step of withdrawing the volume of cerebrospinal fluid includes withdrawing the volume of cerebrospinal fluid into a syringe.

9. The method of claim 1, wherein the step of infusing the volume of cerebrospinal fluid includes exerting a pressure on the volume of cerebrospinal fluid.

10. The method of claim 1, wherein the step of infusing the volume of cerebrospinal fluid is performed at a rate capable of increasing cerebrospinal fluid flow within the cisterna magna space.

11. The method of claim 1, wherein the step of infusing the volume of cerebrospinal fluid is performed at a rate capable of increasing cerebrospinal fluid flow within a ventricular system of a subject.

12. The method of claim 11, wherein the increased cerebrospinal fluid flow within the ventricular system of the subject creates a kinetic energy that transmits to a blood-cerebrospinal fluid barrier of the ventricular system as an electrochemical potential difference.

13. The method of claim 12, wherein the blood-cerebrospinal fluid barrier is a meningeal barrier.

14. The method of claim 12, wherein the blood-cerebrospinal fluid barrier comprises a choroid plexus structure located at a fourth ventricle of the ventricular system.

15. The method of claim 12, wherein the kinetic energy is converted to potential energy.

16. The method of claim 12, further comprising a shift in ions across a plurality of voltage gated ion channels of the blood-cerebrospinal fluid barrier.

17. The method of claim 1, wherein the step of infusing the volume of cerebrospinal fluid is performed by exerting a pressure through a catheter, which transmits a generated kinetic energy to a semi-permeable membrane within a ventricular system of a subject.

18. The method of claim 17, further wherein a cyclical cycle of converting kinetic energy to potential energy increases flow and circulation of cerebrospinal fluid.

19. The method of claim 17, further wherein a pulsatile flow of cerebrospinal fluid propagates a created potential energy and converts the created potential energy into kinetic energy as the pulsatile flow of cerebrospinal fluid circulates.

20. The method of claim 17, further comprising coupling a manometer to the catheter for measuring a pressure reading of cerebrospinal fluid.

* * * * *